US006221346B1

(12) United States Patent
Streels

(10) Patent No.: US 6,221,346 B1
(45) Date of Patent: Apr. 24, 2001

(54) COMPOSITION WITH BASE OF COCONUT OIL AND ITS USE

(76) Inventor: Elisabeth Streels, Rue Waurara 16, B-4480 Engis (BE)

( * ) Notice: Subject to any disclaimer, the term of this patent is extended or adjusted under 35 U.S.C. 154(b) by 0 days.

(21) Appl. No.: 09/367,432
(22) PCT Filed: Feb. 14, 1997
(86) PCT No.: PCT/BE97/00016
 § 371 Date: Aug. 13, 1999
 § 102(e) Date: Aug. 13, 1999
(87) PCT Pub. No.: WO98/35700
 PCT Pub. Date: Aug. 20, 1998
(51) Int. Cl.[7] .............. A61K 7/035; A61K 7/00
(52) U.S. Cl. ............................ 424/69; 424/401
(58) Field of Search .................. 424/59, 401, 69

(56) References Cited

U.S. PATENT DOCUMENTS 4,929,439 * 5/1990 Cotteret et al. .................. 424/59
5,104,656   4/1992 Seth et al. ....................... 424/401
5,472,982  12/1995 Suzuki ............................. 514/567

FOREIGN PATENT DOCUMENTS

WO91/101717  2/1991 (WO) .

* cited by examiner

*Primary Examiner*—Shelley A. Dodson
*Assistant Examiner*—Konata M George
(74) *Attorney, Agent, or Firm*—Hovey, Williams, Timmons & Collins

(57) ABSTRACT

Composition containing cetyl alcohol, coconut oil, polyoxyethylene oleo-linoleic glyceride, possibly water, and possibly other additives and/or pharmaceutically active principle (s), said composition containing in % of dry matter:

a 5 to 15 % polyoxyethylene oleo-linoleic glyceride, and
20 to 40 % cetyl alcohol, the weight ratio coconut oil and other additives and/or pharmaceutically active principle(s)/cetyl alcohol being comprised between 2/1 and 80/15.

37 Claims, No Drawings

COMPOSITION WITH BASE OF COCONUT OIL AND ITS USE

This application is a 371 of PCT BE 97/0016 filed Feb. 14, 1997.

BACKGROUND OF THE INVENTION

1. Field of the Invention

The present invention relates to a composition containing cetyl alcohol, coconut oil, polyoxyethylene oleo-linoleic glyceride, possibly water, and possibly other additives and/or pharmaceutically active principle(s).

2. Description of the Prior Art

A fatty composition containing cetyl alcohol, a fraction of coconut oil and other additives is known by WO 91/01717. This composition is suitable to be mixed with a large amount of an aqueous phase.

However this composition is not suitable for being mixed with essential oils or with preparations containing paraffin or propylene glycol. Furthermore, the aqueous phase of said document has to contain specific additives and has to be heated before being mixed with the fatty phase.

SUMMARY OF THE INVENTION

The present invention relates to a composition containing advantageously one or more active principles and advantageously free of water, which is suitable to be mixed with water with or without additives, for forming a cream or a stable lotion. The composition according to the invention is moreover very stable on a long period of time and allows to avoid degradation of the active principle or agent due to its contact with water during the storage of the composition. The composition of the invention is thus suitable for preparing a cream or a lotion containing the active agent just before its use. Finally, the composition according to the invention, especially when the composition is substantially water free, has an excellent resistance against the rancid growing, even if the composition contains whole or entire coconut oil, and not a specific fractionated coconut oil known under the name Miglyol, fractionated oil known for having a better resistance against the rancid growing than whole (not fractionated) coconut oil.

The composition according to the invention contains a specific additive, namely polyoxyethylene glyceride, i.e. the product of the alcoholysis of a natural vegetal oil by polyoxyethylene glycols. The said additive is in particular a polyoxyethylene oleo-linoleic glyceride or the product of an alcoholysis of a natural corn oil by polyoxyethylene glycols. The composition according to the invention is thus a composition containing cetyl alcohol, coconut oil, polyoxyethylene oleo-linoleic glyceride, possibly water, and possibly other additives and/or pharmaceutically active principle(s), said composition containing in % of dry matter:

5 to 15% polyoxyethylene oleo-linoleic glyceride, and
20 to 40% cetyl alcohol, the weight ratio coconut oil and other additives and/or pharmaceutically active principle(s) or agent(s)/cetyl alcohol being comprised between 2/1 and 80/15. This weight ratio is important for obtaining a good stability of the composition, in particular after addition of an important amount of water.

Preferably, the weight ratio coconut oil and other additives and/or pharmaceutically active principle(s)/cetyl alcohol is comprised between 2/1 and 70/25. According to a particularly advantageous manner, the ratio is comprised between 2.1 and 2.45. According to an embodiment, the composition according to the invention contains in % of dry matter:

5 to 10% polyoxyethylene oleo-linoleic glyceride, and
20 to 35% cetyl alcohol.

Advantageously, the composition according to the invention is prepared without water or substantially without water, the water necessary for its use being added just before its use. The composition contains for example less than 5% by weight water and has the form of a powder suitable to be mixed with an aqueous phase for forming a milk or cream. Preferably, the powder has a particle size lower than 500 $\mu$m, preferably lower than 100 $\mu$m.

According to an embodiment, the composition contains 5 to 95% by weight water, for example 5 to 50% by weight water.

The composition according to the invention contains advantageously one or more pharmaceutically active principles, in the form of essential oil, alcohol extract or hydro-alcohol extract, chlohexidri gluconas, liquid extract, preparation containing propyleneglycol, preparation containing paraffin, preparation containing glycerin soaking product, or a mixture thereof.

The composition according to the invention may contain, in % of dry matter, up to 75% of pharmaceutically active principle(s) or agent(s). As the composition according t the invention can have the form of a powder and as the active principle(s) or agent(s) are advantageously distributed on a homogeneously manner in the powder, the composition can be packed in sachets or bags containing one dose of the active agent(s).

The invention relates also to a process for the preparation of a powder containing at least a pharmaceutically active principle or agent, the said powder being intended to be mixed with an aqueous medium for giving a cream or a milk. In said process:

cetyl alcohol, coconut oil, polyoxyethylene oleo-linoleic glyceride and possibly other additives are mixed in liquid form (for example after heating and melting of the products in solid form at ambient temperature) so as to form a mixture containing less than 5% water, the said mixture is transformed into a powder, and the said powder is mixed with one or more pharmaceutically active agents, and possibly with other additives.

According to an embodiment, the mixture is transformed into a powder after cooling and solidification of the mixture.

According to another possible embodiment, the mixture is transformed into a powder by spraying the mixture in an atmosphere, the temperature of which is lower than the solidification temperature.

Advantageously, the amount of coconut oil is adjusted so that the powder has a weight ratio coconut oil and other additives and/or pharmaceutically active principle(s) or agent(s)/cetyl alcohol comprised between 70/25 and 2/1.

According to embodiments, polyoxyethylene oleo-linoleic glyceride and cetyl alcohol are used in amounts such that the powder contains in % of dry matter:

5 to 10% polyoxyethylene oleo-linoleic glyceride, and
20 to 35% cetyl alcohol.

According to an embodiment, the mixture is transformed into a powder with a particle size lower than 500 $\mu$m, preferably lower than 100 $\mu$m, for example lower than 50 $\mu$m.

Preferably, in a first step, a liquid mixture containing cetyl alcohol, coconut oil, and possibly one or more additives, and in a second step, one or more pharmaceutically active principles or agents premixed with polyoxyethylene oleo-linoleic glyceride, are added to the liquid mixture prepared in the first step.

It would also be possible to prepare, in a first step, a liquid mixture containing cetyl alcohol, coconut oil, polyoxyethylene oleo-linoleic glyceride, and possibly one or more additives, and, in a second step, one or more pharmaceutically active principles are added in liquid form to the liquid mixture prepared in the first step.

For example, one or more pharmaceutically active principles, in the form of essential oil, alcohol extract or hydro-alcohol extract, chlohexidri gluconas, liquid extract, preparation containing propyleneglycol, preparation containing paraffin, preparation containing glycerin soaking product, or a mixture thereof, are used.

DESCRIPTION OF THE PREFERRED EXAMPLES

Examples of embodiment will be described hereafter.

Mixtures according to the invention have been prepared by mixing as liquid, coconut oil, labrafil (polyoxyethylene oleo-linoleic glyceride, corn oil), cetyl alcohol, and possibly glycerin. After cooling of the mixture at room temperature, the mixture was transformed into a powder.

The following table gives the parts in weight of the different compounds used for the preparation of the mixtures:

| Mixture | 1 | 2 | 3 | 4 | 5 | 6 | 7 |
|---|---|---|---|---|---|---|---|
| Coconut oil | 60 | 52 | 60 | 60 | 40 | 55 | 55 |
| Cetyl alcohol | 25 | 27 | 25 | 30 | 25 | 27 | 30 |
| Labrafil | 5 | 6 | 10 | 7 | 6 | 8 | 5 |
| Glycerin | | | | | 19 | 5 | |

The powder had a particle size of about 50 μm.

The powders of the mixtures 1 to 7 have been mixed with essential oils, namely a mixture containing 4.5 parts by weight Rosemary, 6 parts by weight Wintergreen, 6 parts by weight Sage and 7.5 parts by weight Camphor. These powders had excellent life stability.

The composition of the so prepared powders is given in parts by weight in the following table:

| powder | 1 | 2 | 3 | 4 | 5 | 6 | 7 |
|---|---|---|---|---|---|---|---|
| Coconut oil | 60 | 52 | 60 | 60 | 40 | 55 | 55 |
| Cetyl alcohol | 25 | 27 | 25 | 30 | 25 | 27 | 30 |
| Labrafil | 5 | 6 | 10 | 7 | 6 | 8 | 5 |
| Glycerin | | | | | 19 | 5 | |
| Essential oils | 5 | 15 | 5 | 3 | 10 | 5 | 10 |
| Ratio H/A | 65/25 | 67/27 | 65/25 | 63/30 | 69/25 | 65/27 | 65/30 |

Ratio H/A: weight ratio coconut oil and other additive(s) and active agent (s)/cetyl alcohol The so prepared powders have thereafter been mixed with water at room temperature for forming either a cream or milk or a lotion. By adding one part by weight water to one part by weight powder, a cream was obtained, while by adding 5 parts by weight water to one part by weight powder, a lotion was obtained.

Tests have shown that the so prepared creams were not too fatty, were not irritating, and that the formation of crusts could be prevented.

Despite the presence of a large quantity of water, the prepared creams had a texture similar to the structure of the product Nivea.

The creams by mixing of one part by weight of powder and one part by weight water have been mixed with 0.1 part by weight of an antibiotic agent per part by weight of cream or with 1 part by weight of "Merfen"® (per part by weight of cream.

The powder prepared from mixture 2 has been mixed with the following mixtures of essential oils:

Mixture of essential oils n° 1: rosemary 3 g, Wintergreen 5.5 g, camphor 4.5 g and sage 1 g, said mixture of essential oils was mixed with 86 g of the powder of 5 mixture 2.

Mixture of essential oils no 2: rosemary 4.4 g, Wintergreen 6.8 g, Betula 2.8 g and Laurus nobilis 2.8 g, said mixture of essential oils was mixed with 83.2 g of the powder of mixture 2.

Mixture of essential oils n° 3: Calendula 1.2 g, Alcohol at 70% 2.5 g, Rosemary 1.5 g, Lavender 5.5 g, Thyme 1.5 g and sage 1.5 g, said mixture of essential oils was mixed with 86.3 g of the powder of mixture 2.

Mixture of essential oils n° 4: Calendula 1.5 g, Thyme 1.5 g, Lavender 5 g, Neomycin 500,000 U, said mixture of essential oils was mixed with 88.5 g of the powder of mixture 2.

The so prepared compositions had antibiotic and disinfecting properties. It seems from tests that a better efficiency of the treatment could be reached.

On a similar way, powders containing as active agents other essential oils, alcohol extracts or hydro-alcohol extracts, chlohexidri gluconas, liquid extracts, preparations containing propyleneglycol, preparations containing paraffin, preparations containing glycerin soaking product, or mixtures thereof have been prepared. The powder according to the invention can contain up to 15%, possibly much more. Before its use, the powder is transformed into a cream or lotion. The powder is advantageously placed in sachet or bag containing exactly the dose of active agent to be applied on the body or part of the body.

The composition according to the invention, especially in the form of a cream to be applied on the skin, contains possibly other alcohol's, such as ethanol, propanol, isopropanol. It is obvious that the composition of the invention can further contain a surfactant, advantageously an anionic surfactant, preferably an oily excipient (such as an oil) and/or a pharmaceutical and/or cosmetic active agent and/or one or more essential oils and/or one or more perfumes. . . . For example, the composition contains a penetrating agent and/or a revulsive agent and/or a vasodilatator and/or an analgesic.

The invention relates also to an ointment, a cream or a viscous preparation containing a composition according to the invention, a stick or a solid product containing a composition according to the invention, a support (for example a porous support) provided with a layer of a composition according to the invention, a finger cover, a glove or part of a glove provided on its inner face with a layer of a composition according to the invention.

The invention has still as subject matter the use of a composition of the invention for the preparation of compositions having increased efficiency of an active agent applied o the skin of a patient or an animal.

Another subject matter of the invention is a kit comprising a first vial containing a composition of the invention and a second vial containing an active principle or agent or a cosmetic agent, for the simultaneous application or the successive application of the principle and agent, or inversely.

Still another subject matter of the invention is a pharmaceutical preparation for the curative and/or preventive treatment of the skin, said preparation containing a composition of the invention.

The invention has thus also as subject matter the use of coconut oil as active agent in the preparation of compositions for the healing of wounds, vasodilatating compositions, anti-pain compositions.

During the preparation of the compositions of the invention, it has been observed that for treating diseases or troubles, such as osteoarthritis, it was advantageous to use in combination a penetrating agent and other vasodilatating, analgesic, anti inflammatory, decongestant and revulsive agents, in particular to use the combination of the following essential oils: Rosemary, Wintergreen, Sage and Camphor. The invention has thus also as subject matter compositions comprising the essential oils cited hereabove, compositions suitable for the treatment of the skin, the osteoarthritis, . . . These compositions comprise advantageously a composition of the type disclosed in claim 1, but may contain other excipients.

What is claimed is:

1. A composition comprising:

from 20 to 40% by weight of cetyl alcohol calculated with respect to the weight of the water free composition;

from 5 to 15% by weight of polyoxyethylene oleo-linoleic glyceride
       calculated with respect to the weight of the water free composition; and coconut oil, wherein the weight ratio of said coconut oil to said cetyl alcohol is from 2:1 to 80:15.

2. The composition of claim 1, wherein said weight ratio is from 2:1 to 70:25.

3. The composition of claim 1, said composition comprising from 5 to 10% by weight of polyoxyethylene oleo-linoleic glyceride calculated with respect to the weight of the water free composition and from 20 to 35% by weight of cetyl alcohol calculated with respect to the weight of the water free composition.

4. The composition of claim 1, said composition comprising less than 5% by weight of water.

5. The composition of claim 1, said composition being a powder.

6. The composition of claim 5, said powder having an average particle size of less than 500 μm.

7. The composition of claim 6, said powder having an average particle size of less than 100 μm.

8. The composition of claim 1, said composition comprising from 5 to 95% by weight water.

9. The composition of claim 1, said composition comprising from 5 to 50% by weight water.

10. A process for the preparation of a composition comprising the steps of:

(a) forming a mixture comprising:
       the liquid form of from 5 to 15% by weight on a dry basis of polyoxyethylene oleo-linoleic glyceride calculated with respect to the weight of the water free mixture;
       the liquid form of from 20 to 40% by weight on a dry basis of cetyl alcohol calculated with respect to the weight of the water free mixture; and
       coconut oil,
       wherein said mixture comprises less than 5% by weight water and the weight ratio of said coconut oil to said cetyl alcohol is from 2:1 to 80:15; and (b) converting said mixture to a powder.

11. The process of claim 10, wherein step (b) comprises converting said mixture to a powder after cooling and solidification of said mixture.

12. The process of claim 10, wherein step (b) comprises converting said mixture to a powder by spraying said mixture in an atmosphere having a temperature below the solidification temperature of said mixture.

13. The process of claim 10, wherein said weight ratio is from 2:1 to 70:25.

14. The process of claim 10, wherein step (a) comprises from 5 to 10% of polyoxyethylene oleo-linoleic glyceride calculated with respect to the weight of the water free composition and from 20 to 35% of cetyl alcohol calculated with respect to the weight of the water free mixture.

15. The process of claim 10, wherein said powder has a particle size of less than 500 μm.

16. The process of claim 15, wherein said powder has a particle size of less than 100 μm.

17. A composition comprising:

from 20 to 40% by weight of cetyl alcohol calculated with respect to the weight of the water free composition;

from 5 to 15% by weight on a dry basis of polyoxyethylene oleo-linoleic glyceride calculated with respect to the weight of the water free mixture;

coconut oil; and an ingredient selected from the group consisting of additives, pharmaceutically active agents, and mixtures thereof, wherein the weight ratio of the total weight of said coconut oil and said ingredient to the weight of said cetyl alcohol is from 2:1 to 80:15.

18. The composition of claim 17, wherein said weight ratio is from 2:1 to 70:25.

19. The composition of claim 17, said composition comprising from 5 to 10% by weight of polyoxyethylene oleo-linoleic glyceride calculated with respect to the weight of the water free composition and from 20 to 35% by weight of cetyl alcohol calculated with respect to the weight of the water free composition.

20. The composition of claim 17, said composition comprising less than 5% by weight of water.

21. The composition of claim 17, said composition comprising 5 to 95% by weight water.

22. The composition of claim 17, said composition comprising 5 to 50% by weight water.

23. The composition of claim 17, said composition being a powder.

24. The composition of claim 23, said powder having an average particle size of less than 500 μm.

25. The composition of claim 24, said powder having an average particle size of less than 100 μm.

26. The composition of claim 17, wherein said ingredient is a pharmaceutically active agent selected from the group consisting of essential oils, alcohol extracts, hydro-alcohol extracts, chlohexidri gluconas, liquid extracts, propyleneglycol-containing preparations, paraffin-containing preparations, preparations containing glycerin soaking product, and mixtures thereof.

27. The composition of claim 26, wherein said pharmaceutically active agent is present in said composition at a level of up to 15% by weight calculated with respect to the weight of the water free composition.

28. A process for the preparation of a composition comprising the steps of:
  (a) forming a mixture comprising:
    the liquid form of from 20 to 40% by weight of cetyl alcohol calculated with respect to the weight of the water free mixture;
    the liquid form of from 5 to 15% by weight of polyoxyethylene oleo-linoleic glyceride calculated with respect to the weight of the water free mixture; and
    the liquid form of coconut oil,
    wherein said mixture comprises less than 5% by weight of water;
  (b) converting said mixture to a powder; and
  (c) mixing said powder with an ingredient selected from the group consisting of additives, pharmaceutically active agents, and mixtures thereof, wherein the weight ratio of the total weight of said coconut oil and said ingredient to the weight of said cetyl alcohol is from 2:1 to 80:15.

29. The process of claim 28, wherein step (b) comprises converting said mixture to a powder after cooling and solidification of said mixture.

30. The process of claim 28, wherein step (b) comprises converting said mixture to a powder by spraying said mixture in an atmosphere having a temperature below the solidification temperature of said mixture.

31. The process of claim 28, wherein said weight ratio is from 2:1 to 70:25.

32. The process of claim 28, wherein step (a) comprises from 5 to 10% by weight of polyoxyethylene oleo-linoleic glyceride calculated with respect to the weight of the water free mixture and from 20 to 35% by weight of cetyl alcohol calculated with respect to the weight of the water free mixture.

33. The process of claim 28, wherein the powder resulting from step (b) has an average particle size of less than 500 $\mu$m.

34. The process of claim 33, wherein the powder resulting from step (b) has an average particle size of less than 100 $\mu$m.

35. The process of claim 28, wherein step (a) comprises forming a first mixture comprising said cetyl alcohol and said coconut oil, forming a second mixture comprising said pharmaceutically active agent and said polyoxyethylene oleo-linoleic glyceride and adding said second mixture to said first mixture.

36. The process of claim 28, wherein step (a) comprises adding forming a mixture comprising said cetyl alcohol, said polyoxyethylene oleo-linoleic glyceride and said coconut oil, and adding said pharmaceutically active agent to said mixture.

37. The process of claim 28, wherein said ingredient is a pharmaceutically active agent selected from the group consisting of essential oils, alcohol extracts, hydro-alcohol extracts, chlorhexidri gluconas, liquid extracts, propyleneglycol-containing preparations, paraffin-containing preparations, preparations containing glycerin soaked product, and mixtures thereof.

* * * * *